(12) United States Patent
Hefner et al.

(10) Patent No.: US 8,475,110 B2
(45) Date of Patent: Jul. 2, 2013

(54) SYSTEM AND METHOD FOR ONLINE MONITORING OF CORROSION OF GAS TURBINE COMPONENTS

(75) Inventors: Rebecca Hefner, Greenville, SC (US); Jeff P. Czapiewski, Greer, SC (US)

(73) Assignee: General Electric Company, Schenectady, NY (US)

( * ) Notice: Subject to any disclaimer, the term of this patent is extended or adjusted under 35 U.S.C. 154(b) by 623 days.

(21) Appl. No.: 12/512,618

(22) Filed: Jul. 30, 2009

(65) Prior Publication Data
US 2011/0027063 A1 Feb. 3, 2011

(51) Int. Cl.
*F01D 21/10* (2006.01)
*F01D 25/00* (2006.01)

(52) U.S. Cl.
USPC .......... 415/1; 415/116; 415/118; 416/61; 134/18; 134/22.18; 134/34; 324/700; 204/404; 205/775.5; 205/776.5; 205/777

(58) Field of Classification Search
USPC ............ 415/1, 118, 116; 416/1, 61; 134/18, 134/22.1, 22.18, 2, 3, 34; 324/700; 204/404; 205/775.5, 776, 776.5, 777
See application file for complete search history.

(56) References Cited

U.S. PATENT DOCUMENTS

| | | | |
|---|---|---|---|
| 4,509,332 A | | 4/1985 | Bellows |
| 4,808,235 A * | | 2/1989 | Woodson et al. .......... 134/22.19 |
| 5,193,976 A * | | 3/1993 | Kolev et al. ................. 415/116 |
| 5,594,665 A * | | 1/1997 | Walter et al. ................ 700/301 |
| 6,628,111 B2 * | | 9/2003 | Shapiro et al. ............. 324/71.2 |
| 6,683,463 B2 | | 1/2004 | Yang et al. |
| 7,180,309 B1 | | 2/2007 | Yang |
| 7,309,414 B2 | | 12/2007 | Yang |
| 7,535,565 B1 | | 5/2009 | Viertl et al. |
| 7,678,260 B1 * | | 3/2010 | Yang et al. .................. 205/775.5 |
| 2005/0274628 A1 | | 12/2005 | Yang |
| 2006/0056959 A1 * | | 3/2006 | Sabol et al. ................... 415/118 |
| 2007/0193887 A1 * | | 8/2007 | Tormoen et al. ........... 205/775.5 |

FOREIGN PATENT DOCUMENTS
WO 02077615 A2 10/2002

OTHER PUBLICATIONS

Extended European Search Report issued in connection with EP 10170341.1, Oct. 28, 2010.

* cited by examiner

*Primary Examiner* — Christopher Verdier
(74) *Attorney, Agent, or Firm* — Ernest G. Cusick; Gary M. Hartman; Domenica N. S. Hartman

(57) ABSTRACT

A system and method capable of performing online corrosion monitoring of a component installed in a gas turbine. A sensing device is located so that electrodes thereof are exposed to an operating environment within the gas turbine section containing the component. The electrodes are formed of a material so that the component and electrodes similarly respond to corrosive agents within the gas turbine section. The electrodes are electrically insulated from each other and each electrode is operable as an anodic electrode or a cathodic electrode, depending on the extent of corrosion thereat, so that each electrode has an electrical potential value, voltages exist across the electrodes, electric currents flow between the electrodes, and the electrical potential/current values correspond to corrosion behaviors at the anodic electrodes. During gas turbine operation, output signals are obtained from the sensing device and indications are provided as to when certain maintenance operations should be performed on the gas turbine.

11 Claims, 3 Drawing Sheets

SYSTEM AND METHOD FOR ONLINE MONITORING OF CORROSION OF GAS TURBINE COMPONENTS

BACKGROUND OF THE INVENTION

The present invention generally relates to corrosion monitoring technology, and more particularly to a method and system for online corrosion monitoring of turbomachinery components, such as blades within a compressor section of a gas turbine.

Components of turbomachines, including those of gas turbines employed for power generation and propulsion, are subject to damage from corrosion, oxidation, and contamination by agents present in the airflow of the turbomachine during its operation. For example, in corrosive environments such as near and offshore regions and industrial facilities, gas turbine compressors may suffer relatively high pitting corrosion rates due to water condensation on the blades of their first several stages, combined with fouling deposits and chloride and/or sulfate air pollutants. To maintain compressor health, industrial gas turbine operators perform various maintenance actions, typically including online and/or offline water washes, offline inspections, and filter maintenance. Understandably, disadvantages exist if these tasks are performed too frequently or infrequently. For example, excessive online washing can promote erosion, while insufficient online washing results in increased corrosion rates due to buildup of corrosive agents on the compressor blades. Inevitably, offline inspections must be performed, requiring turbine shutdown and dismantlement that incur downtime. Though offline inspections are very costly events, failing to timely perform these inspections can result in damage to the turbine, such as from liberation of a compressor blade due to pitting corrosion. Consequently, gas turbine operators rely on carefully scheduled offline inspections to monitor compressor health and perform repairs to avert destructive events.

Complete results from offline inspections are often unavailable for several months, and can be difficult to directly correlate to actual compressor corrosion/pitting rates present in the compressor. Therefore, it would be desirable to minimize offline inspections by providing turbine operators with realtime information on the compressor status, such that appropriate maintenance activities can be taken when and as necessary to prolong compressor life in corrosive environments. However, many factors complicate efforts to determine through online monitoring the presence and extent of corrosion on compressor components of industrial gas turbines. Complicating factors include the operating parameters of the machine, washing intervals and methods, filter type and maintenance, and various other variables. For many industrial gas turbines, filter maintenance and failure, seal leakage, and emissions from neighboring facilities can have a significant and unpredictable impact on corrosion rates. Other conditions that can affect corrosion rates include the operational parameters of the compressor, such as turndown, startup/shutdown amount, etc.

From the above, it can be appreciated that, to avoid reliance on confusing operational and environmental indicators for the purpose of making timely operational and inspection decisions, gas turbine operators would require realtime (online) measurements of corrosion rates of the gas turbine components, and a comprehensive set of maintenance instructions based on those measurements.

BRIEF DESCRIPTION OF THE INVENTION

The present invention generally provides a system and method capable of performing online monitoring of corrosion of a component installed in a section of an operating gas turbine, for example, the blades of an industrial gas turbine compressor.

According to a first aspect of the invention, the method generally includes locating a multi-electrode array sensing device on the gas turbine so that electrodes of the sensing device are exposed to an operating environment within the section of the gas turbine. The electrodes are formed of a material so that the component and the electrodes similarly respond to corrosive agents within the section of the gas turbine containing the component to be monitored. The electrodes are electrically insulated from each other and each electrode is operable as an anodic electrode or a cathodic electrode, depending on the extent of corrosion at the electrode. As a result, each electrode has an electrical potential value, voltages exist across the electrodes, and an electrical current flows from each anodic electrode to at least one of the cathodic electrodes. The electrical potential values and the electric current values correspond to corrosion behaviors at the anodic electrodes. While the gas turbine is operating, output signals are obtained from the sensing device based on the electrical potential values and/or the electric current values, and indications as to when maintenance operations should be performed on the gas turbine are provided by using the output signals of the sensing device to predict a corrosion characteristic of the component.

According to a second aspect of the invention, the system includes a multi-electrode array sensing device located on the gas turbine so that electrodes of the sensing device are exposed to an operating environment within the section of the gas turbine containing the component to be monitored. The electrodes are formed of an electrode material and the component is formed of a component material so that the component and electrodes similarly respond to corrosive agents within the section of the gas turbine. The electrodes are electrically insulated from each other and each electrode is operable as an anodic electrode or a cathodic electrode, depending on the extent of corrosion thereat. As a result, each electrode has an electrical potential value, voltages exist across the electrodes, and an electrical current flows from each anodic electrode to at least one of the cathodic electrodes. Furthermore, the electrical potential values and the electric current values correspond to corrosion behaviors at the anodic electrodes. The system further includes equipment for obtaining output signals from the sensing device based on the electrical potential values and/or current values, and equipment for indicating when a maintenance operation should be performed on the gas turbine by using the output signals of the sensing device to predict a corrosion characteristic of the component.

The system and method of this invention are preferably capable of providing gas turbine operators with realtime measurements of corrosion rates within a particular section of a gas turbine, such that timely operational and inspection decisions can be made without relying solely on operational and environmental indicators. From these measurements, the system and method are preferably capable of providing gas turbine operators with a comprehensive set of maintenance instructions, such that the need and timing of offline inspections can be more accurately predicted.

Other aspects and advantages of this invention will be better appreciated from the following detailed description.

DETAILED DESCRIPTION OF THE INVENTION

Figure 1:
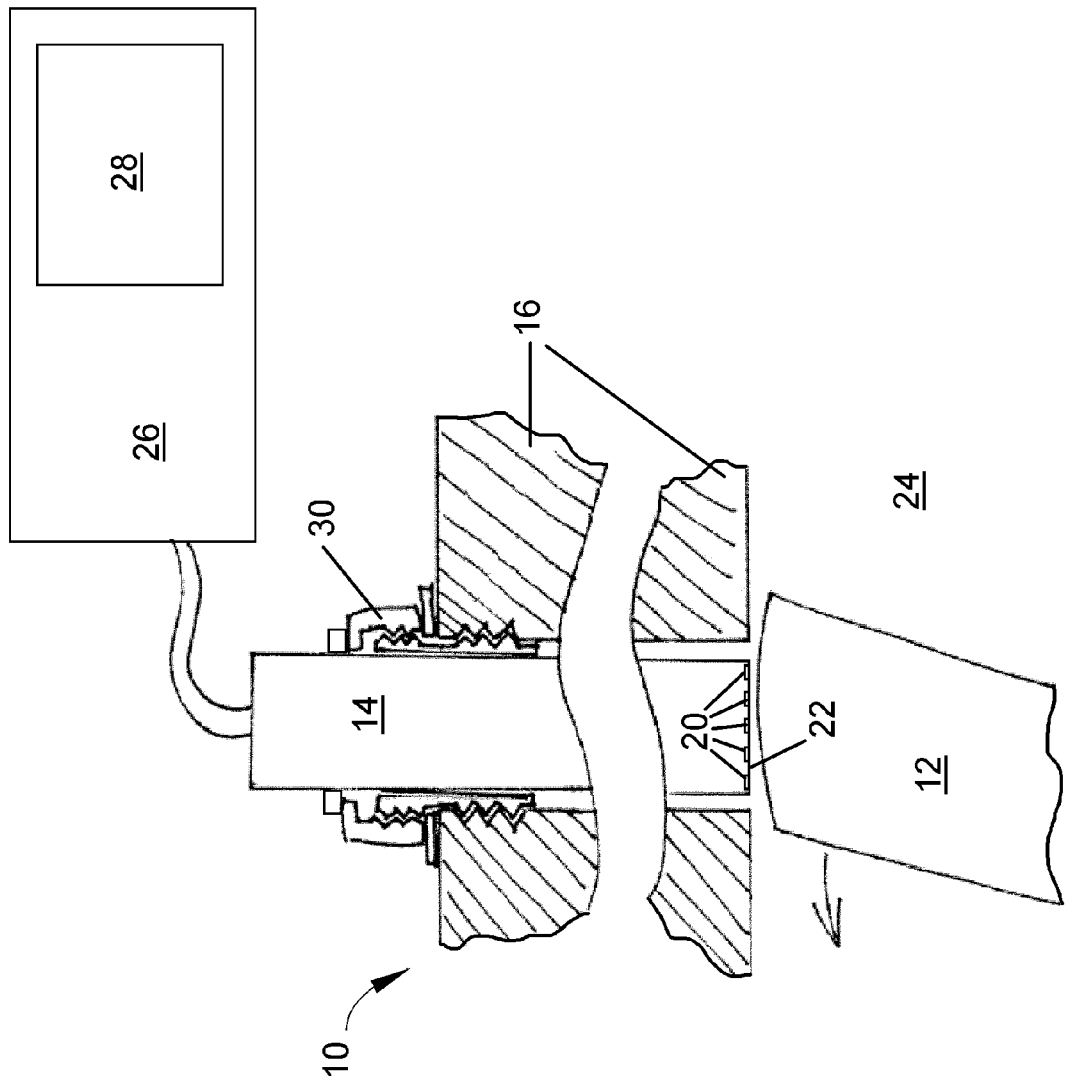
FIG. 1 schematically represents a corrosion monitoring sensor installed through the shell wall of an industrial gas turbine compressor in accordance with a first embodiment of the invention.

The present invention will be described in reference to turbine components of a turbomachine, and particularly compressor blades within the compressor section of an industrial gas turbine used for power generation, though it should be understood that the invention could be adapted for use with gas turbines used in propulsion applications, as well as various other applications in which corrosion characteristics of a component are not readily predictable due to variations in operating environment and conditions. For purposes of discussion, a fragmentary view of a compressor section 10 of an industrial gas turbine is represented in FIG. 1. The compressor section 10 contains compressor blades 12, of which the tip region of one such blade 12 is represented in FIG. 1. The blades 12 may be formed of a variety of materials, notable examples of which include series 400 martensitic stainless steels such as AISI 403 and 403 Cb, and precipitation-hardened martensitic stainless steels such as GTD-450 (nominally by weight, 15.5% Cr, 6.3% Ni, 0.8% Mo, 0.03% C, balance Fe), though other metal alloys could be used. The surfaces of the blades 12 are subjected to corrosion as a result of moisture that typically contains salts and acids and collects on the blades 12. During operation of an industrial gas turbine, the use of evaporative coolers, condensation resulting from humid air being accelerated at the compressor inlet, and rain can result in the accumulation of moisture on the blades 12, especially those within the first several stages of the compressor section. Corrosion can also occur as a result of moisture that accumulates on the blades 12 while the gas turbine is not operating.

For the purpose of monitoring corrosion of the blades 12 and other components within the compressor section 10, FIG. 1 shows a sensor 14 mounted to the shell wall 16 of the compressor section 10. In particular, the sensor 14 is shown inserted into an opening 18 in the wall 16, such as an existing sight hole port used to inspect the compressor section 10 with a borescope probe, though other mounting methods could be used. The sensor 14 is shown with one end protruding from the exterior side of the shell wall 16 and secured by a swage-lock-type compression fitting 30, though other means for securing the sensor 14 are foreseeable. The oppositely-disposed inward end of the sensor 14 is portrayed as mounted substantially flush with the interior surface of the shell wall 16, with multiple electrodes 20 defined on its face 22. Though a single row of electrodes 20 is visible in FIG. 1, the electrodes 20 are preferably arranged in a two-dimensional array, with the end face of each electrode 20 exposed to the environment within the interior 24 of the compressor section 10. The electrodes 20 are insulated from each other, and therefore are not directly electrically connected to each other. The sensor 14 is represented in FIG. 1 as connected by a cable to a computer 26 or other suitable processing equipment, so that the output of the sensor 14 can be manipulated, stored and displayed, such as with the screen 28 represented in FIG. 1. The computer 26 is preferably capable of analyzing the output of the sensor 14 in real time and saving the data for future evaluation. Various commercial software packages for performing these operations are known and available for programming the computer 26, and therefore will not be discussed in any detail here.

The sensor 14 is configured as a coupled multi-electrode array sensor (CMAS), and is intended to measure corrosion behavior, preferably both corrosion rates and pitting depth. For this purpose, the sensor 14 measures localized corrosion behavior within the compressor section 10 based on electrochemical reactions that occur on the exposed faces of the electrodes 20 as a result of corrosion. Because the electrodes 20 are insulated from each other, the sensor 14 is adapted to generate electrical potentials between the electrodes 20 and/or electric current flow between the electrodes 20 as a result of the electrodes 20 being at different electrochemical potentials. Whether current flows from or to a given electrode 20 will depend on whether the electrode 20 is behaving as an anode (losing electrons) or a cathode (gaining electrons) within the electrochemical reaction associated with corrosion. Spacing between adjacent electrodes 20 can vary, with optimal spacing being ascertainable through routine experimentation.

In order to exhibit corrosion behavior similar to the blades 12, the electrodes 20 are formed of a material having corrosion characteristics similar to the material of the blades 12, and more particularly exhibits a similar response to corrosive agents most responsible for corrosion within the compressor section 10 of the gas turbine. For example, the electrodes 20 may be formed of a similar alloy or the very same alloy as the blades 12. In other words, the blades 12 and electrodes 20 have compositions that are preferably within the same commercial specification range for the given alloy. As a result, during operation of the gas turbine, the output signals from the sensor 14 not only indicate the corrosion behavior of the electrodes 20, but by appropriately choosing the electrode material, can be used to predict one or more corrosion characteristics of the blades 12. It is also within the scope of the invention to form the electrodes 20 from an alloy with more sensitivity to corrosive agents within the compressor section 10 to increase the signal response of the sensor 14.

Sensors of the type described above are known in the art, as exemplified by U.S. Pat. Nos. 6,683,463 and 7,309,414 and U.S. Published Patent Application No. 2007/0193887, whose contents are noted regarding the construction, operation and use of such sensors. In a preferred embodiment of the invention, a sensor of this type is specifically adapted for use in a gas turbine compressor, and interpretations of its output are assigned to indicate that certain maintenance actions should be performed on the gas turbine, and particularly the blades 12 within its compressor section 10. For this purpose, for a particular type of gas turbine, transfer functions must be developed relating either the voltage-based and/or current-based output signal of the sensor 14 to corrosion characteristics of the blades 12 within the compressor section 10 of the gas turbine. The development of suitable transfer functions is generally within the capability of those skilled in the art, and therefore will not be discussed in any detail here.

Figure 3:
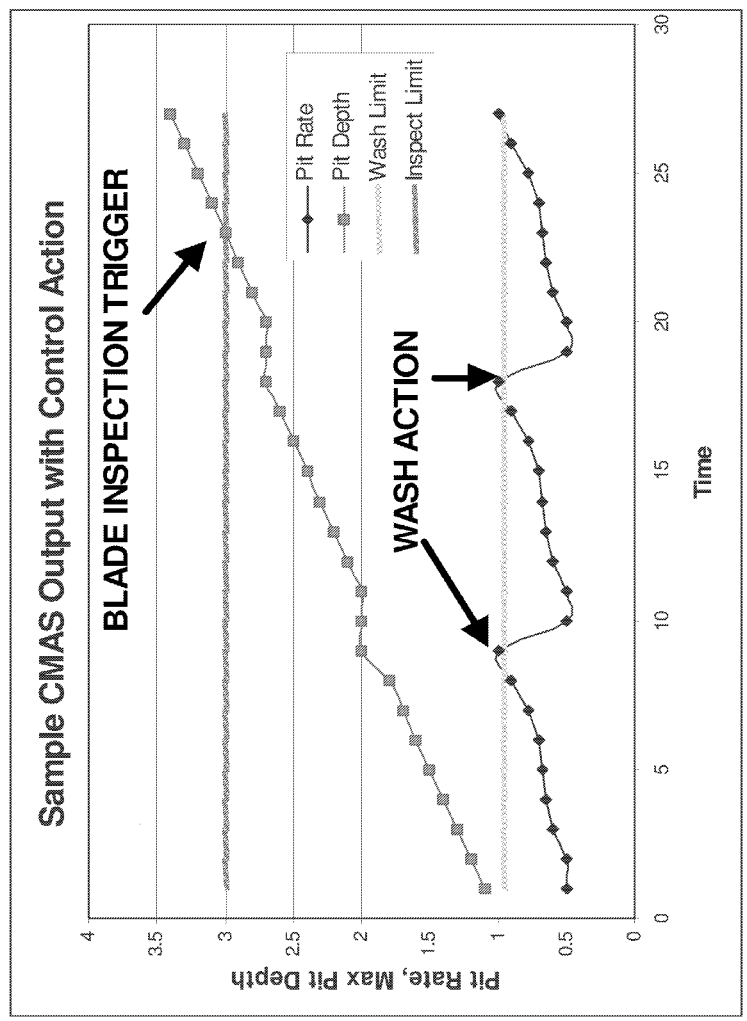
FIG. 3 is a graph representing outputs of the sensor of either FIG. 1 or 2, and indicated control actions to be taken based on the outputs.

Of particular significance is the interpretation of the output of the sensor 14 with respect to corrosion behavior within the compressor section 10, and the assignment of certain maintenance actions that should be performed on the gas turbine as a result of interpreting the sensor output as indicative of corrosion rates and status (for example, pitting depth). Based on appropriate empirical or theoretical modeling of the gas turbine, the computer 26 can be employed to predict corrosion rates on the blades 12 by monitoring the current flow between and/or the voltages across the electrodes 20. For example, general (average) corrosion rates can be predicted based on the average of the currents between the anodic and cathodic electrodes 20, and maximum or localized corrosion rates can be predicted based on the fastest corroding electrode 20, i.e., the most anodic electrode 20 from which electrons are lost at the highest rate. Corrosion depth on the blades 12 can also be predicted based on anodic charges at the anodic electrodes 20 or by back-calculating metal loss at the anodic electrodes 20 via counting the flowing electrons (measure current). By associating the sensor outputs with corrosion behavior in this manner, the computer 26 can be further used to indicate when a maintenance operation should be performed on the gas turbine. For example, FIG. 3 is representative of a screen shot of the computer display 28, in which a graph is displayed plotting pitting depth and pitting rate against time. Two limits are indicated on the graph, a first being a corrosion rate limit which in the example is arbitrarily set at one micrometer per time unit, and the second being a pitting depth limit which in the example is arbitrarily set at three micrometers. In the example, the corrosion rate limit provides an indication that, if exceeded, an online or offline water wash should be performed. Also in the example, the pitting depth limit provides an indication that, if exceeded, the gas turbine should be shut down and a visual inspection performed. The slope of the corrosion rate data can also be monitored to identify any operating conditions or events that may have occurred which would warrant further investigation. By combining the sensor measurements with other available data, such as turbine operating hours, temperatures, etc., it may also be possible to predict the life of the blades 12 within the compressor section 10 based on the amount of corrosion predicted for the blades 12. Additionally, the sensor data could provide valuable life prediction tools for compressor blades of future machines, for example, by cross referencing corrosion rates with filter configurations, washing practices, environment class, humidity, etc.

Figure 2:
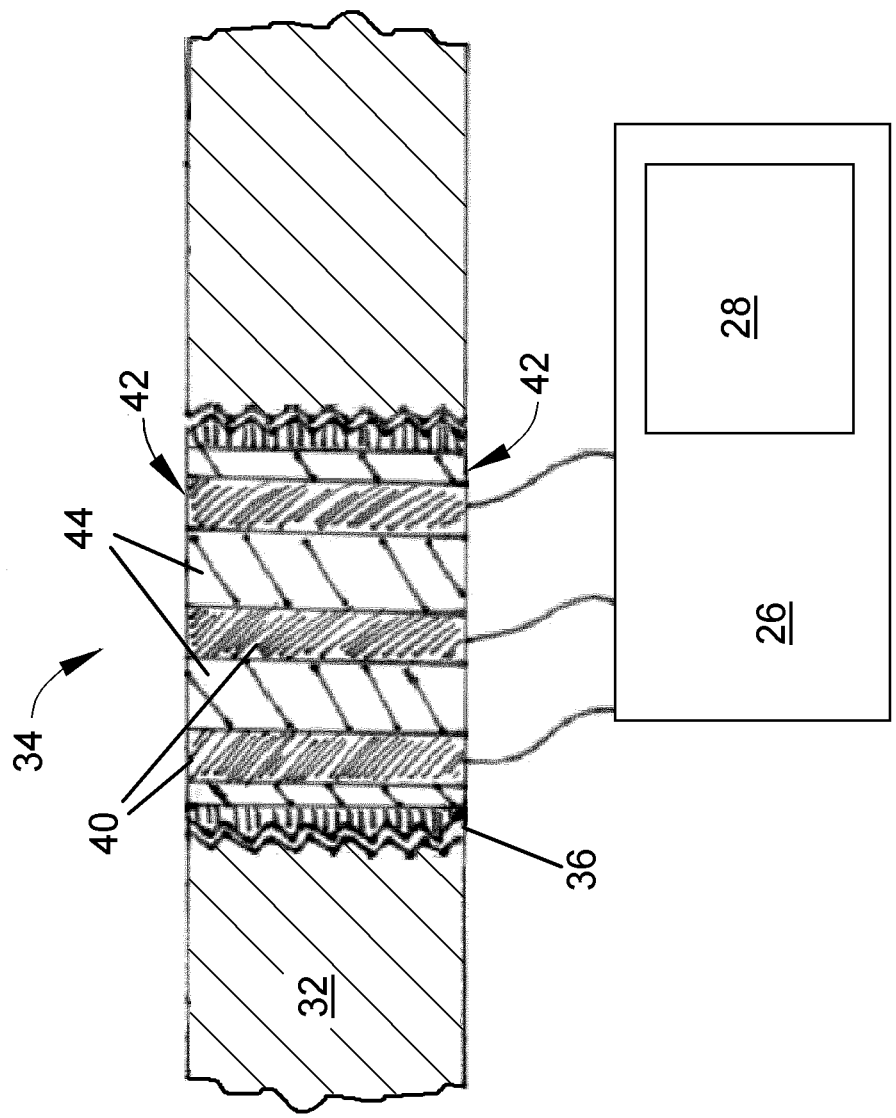
FIG. 2 schematically represents a corrosion monitoring sensor installed in a compressor blade of an industrial gas turbine in accordance with a second embodiment of the invention.

Whereas the embodiment represented in FIG. 1 shows the sensor 14 inserted in an existing opening 18 in a compressor shell wall 16, other configurations are foreseeable and within the scope of the invention. For example, in FIG. 2 a planarized sensor 34 is represented generally in accordance with U.S. Published Patent Application No. 2007/0193887. The sensor 34 is shown embedded in a compressor blade 32 and secured by a screw-type fitting 36, though other means for securing the sensor 34 are foreseeable. The sensor 34 defines opposite faces 42 that are substantially flush with suction and pressure surfaces of the blade 32. Similar to the embodiment of FIG. 1, the sensor 34 comprises a two-dimensional array of individual electrodes 40, each exposed at least one face 42 of the sensor 34. As shown in FIG. 2, the electrodes 40 are embedded in and separated by a structure 44 formed of a dielectric material, such as a ceramic, so that the ends of the electrodes 40 are exposed to the environment within the compressor section containing the blade 32. By coupling the sensor 34 to the computer 26 as represented in FIG. 2, the sensor 34 is capable of operating in the same manner as described for the sensor 14 of FIG. 1.

In view of the above, the sensors 14 and 34 and computer 26 are adapted to cooperate for the purpose of providing continuous, realtime monitoring of localized and general (average) corrosion and corrosion rates in a gas turbine compressor. The computer 26 can be programmed to provide maintenance instructions that are triggered by output signals generated by the sensors 14 and 34 and tailored to suggest appropriate actions based on the type and level of the sensor output. Appropriate actions include, but are not limited to, preemptive washing of corrosive fouling to extend blade life, preemptive washing of corrosive fouling to prevent efficiency drops, alerting of site specific issues such as filter leaks/failures and local corrosive emissions, scheduled blade inspections/replacements, monitoring of downtime corrosion, etc. As a result, the sensors 14 and 34 and computer 26 are capable of providing proactive maintenance options that, if followed, can avoid compressor blade liberations that might otherwise occur as a result of pitting corrosion.

While the invention has been described in terms of specific embodiments, it is apparent that other forms could be adopted by one skilled in the art. For example, the physical configuration of the sensors 14 and 34 could differ from that shown, and materials and processes other than those noted could be used. Therefore, the scope of the invention is to be limited only by the following claims.

The invention claimed is:

1. A method for online monitoring of corrosion of a component installed in a section of a gas turbine, the method comprising:

locating a multi-electrode array sensing device on the gas turbine so that the sensing device is mounted in a wall of a second component of the gas turbine that is spaced apart from the first component, a face of the sensing device is substantially flush with a surface of the second component, and electrodes at the face of the sensing device are exposed to an operating environment within the section of the gas turbine, the electrodes being formed of an electrode material and the first component being formed of a component material that respond to at least one corrosive agent within the section of the gas turbine, the electrodes being electrically insulated from each other and each electrode being operable as an anodic electrode or a cathodic electrode depending on the extent of corrosion thereat so that each electrode has an electrical potential value, voltages exist across the electrodes, an electrical current flows from each anodic electrode to at least one of the cathodic electrodes, and the electrical potential values and the electric current values correspond to corrosion behaviors at the anodic electrodes that occur in response to the electrodes being exposed to the operating environment within the section of the gas turbine engine;

operating the gas turbine and, while the gas turbine is operating, obtaining output signals from the sensing device based on the electrical potential values and the electric current values;

monitoring corrosion characteristics based on the output signals of the sensing device, a first of the corrosion characteristics being pitting rate based on the electric current values and being monitored in relation to a pitting rate limit, a second of the corrosion characteristics being a pitting depth based on the electrical potential or electric current values and being monitored in relation to a pitting depth limit; and indicating when a wash maintenance operation should be performed on the gas turbine in response to the pitting rate exceeding the pitting rate limit, and indicating when a shutdown maintenance operation of the gas turbine should be performed in response to the pitting depth exceeding the pitting depth limit.

2. The method according to claim 1, further comprising the step of performing the wash or shutdown maintenance operation following the indicating step.

3. The method according to claim 2, wherein the maintenance operation is the shutdown maintenance operation and comprises shutdown of the gas turbine and dismantling the first component from the section of the gas turbine.

4. The method according to claim 2, wherein the maintenance operation is the wash maintenance operation and comprises online washing of the section of the gas turbine while the gas turbine is operating.

5. The method according to claim 2, wherein the maintenance operation is the shutdown maintenance operation and comprises shutdown of the gas turbine and offline washing of the section of the gas turbine.

6. The method according to claim 1, wherein the electrode and component materials are the same so that the first component and the electrodes similarly respond to the at least one corrosive agent.

7. The method according to claim 1, wherein the electrode material is more sensitive to the at least one corrosive agent than is the component material.

8. The method according to claim 1, wherein the section of the gas turbine is the compressor section and the first component is a compressor blade.

9. The method according to claim 8, wherein the sensing component is a shell wall of the compressor section and is located in a sight hole port in the shell wall.

10. The method according to claim 1, wherein the monitoring step comprises:
   monitoring the pitting rate as an average corrosion rate based on an average of the electrical currents between the anodic and cathodic electrodes; and
   monitoring the pitting depth as a maximum or localized corrosion rate based on a fastest corroding of the electrodes.

11. A method for online monitoring of corrosion of a compressor blade installed in a compressor section of a gas turbine, the method comprising:
   locating a multi-electrode array sensing device in the compressor section so that the sensing device is mounted in a shell wall of the compressor section, the shell wall is spaced apart from the blade, a face of the sensing device is substantially flush with an inner surface of the shell wall, and electrodes disposed at the face of the sensing device are exposed to an operating environment within the compressor section of the gas turbine, the electrodes being formed of an electrode material and the blade being formed of a blade material so that the blade and the electrodes similarly respond to corrosive agents within the compressor section of the gas turbine, the electrodes being electrically insulated from each other and each electrode being operable as an anodic electrode or a cathodic electrode depending on the extent of corrosion thereat so that each electrode has an electrical potential value, voltages exist across the electrodes, an electrical current flows from each anodic electrode to at least one of the cathodic electrodes, and the electrical potential values and the electric current values correspond to corrosion behaviors at the anodic electrodes that occur in response to the electrodes being exposed to the operating environment within the section of the gas turbine engine;
   operating the gas turbine and, while the gas turbine is operating, obtaining output signals from the sensing device based on the electrical potential values and the electric current values;
   monitoring corrosion characteristics based on the output signals of the sensing device, a first of the corrosion characteristics being pitting rate based on the electric current values and being monitored in relation to a pitting rate limit, a second of the corrosion characteristics being a pitting depth based on the electrical potential values and being monitored in relation to a pitting depth limit;
   indicating when a wash maintenance operation should be performed on the gas turbine in response to the pitting rate based on the electric current values exceeding the pitting rate limit, and indicating when a shutdown maintenance operation of the gas turbine should be performed in response to the pitting depth based on the electrical potential values exceeding the pitting depth limit; and
   performing the wash or shutdown maintenance operation based on the indicating step.

* * * * *